(12) United States Patent
Naito

(10) Patent No.: US 9,622,648 B2
(45) Date of Patent: Apr. 18, 2017

(54) INSERTION DEVICE

(71) Applicant: OLYMPUS CORPORATION, Tokyo (JP)

(72) Inventor: Kimihiko Naito, Kawasaki (JP)

(73) Assignee: OLYMPUS CORPORATION, Tokyo (JP)

( * ) Notice: Subject to any disclaimer, the term of this patent is extended or adjusted under 35 U.S.C. 154(b) by 191 days.

(21) Appl. No.: 14/603,497

(22) Filed: Jan. 23, 2015

(65) Prior Publication Data

US 2015/0196191 A1    Jul. 16, 2015

Related U.S. Application Data

(63) Continuation of application No. PCT/JP2014/062710, filed on May 13, 2014.

(30) Foreign Application Priority Data

May 30, 2013  (JP) ................................. 2013-113936

(51) Int. Cl.
*A61B 1/04* (2006.01)
*A61B 1/00* (2006.01)
*G02B 23/24* (2006.01)

(52) U.S. Cl.
CPC ........ *A61B 1/0016* (2013.01); *A61B 1/00071* (2013.01); *A61B 1/00156* (2013.01); *G02B 23/2476* (2013.01); *A61B 1/00066* (2013.01); *A61B 1/00135* (2013.01)

(58) Field of Classification Search
CPC ............ A61B 1/00066; A61B 1/00133; A61B 1/00147; A61B 1/00156; A61B 1/0016; A61B 1/0052; A61B 1/00055; A61B 5/7455
See application file for complete search history.

(56) References Cited

U.S. PATENT DOCUMENTS

2012/0029281 A1    2/2012  Frassica et al.

FOREIGN PATENT DOCUMENTS

| JP | 2000-111806 A | 4/2000 |
| JP | 2001-78954 A | 3/2001 |
| JP | 2005-279119 A | 10/2005 |

(Continued)

OTHER PUBLICATIONS

English translation of International Preliminary Report on Patentability dated Dec. 10, 2015 together with the Written Opinion received in related International Application No. PCT/JP2014/062710.

(Continued)

*Primary Examiner* — Alexandra Newton
(74) *Attorney, Agent, or Firm* — Scully, Scott, Murphy & Presser, P.C.

(57) ABSTRACT

An insertion device includes a movement section provided in an inserting section or an attachment unit attached to the inserting section, and moving to cause a propulsive force to act on the inserting section, a holdable grip provided to a proximal direction side with respect to the inserting section, and a driving source driven so as to generate a movement driving force to move the movement section. The insertion device includes a base member to which the grip is abutted, and a coupling member including a driving source-side abutting surface to which an outer peripheral surface of the driving source is abutted, and coupling the driving source to the base member.

15 Claims, 9 Drawing Sheets

(56) References Cited

FOREIGN PATENT DOCUMENTS

| | | |
|---|---|---|
| JP | 2005-288035 A | 10/2005 |
| JP | 2009-189653 A | 8/2009 |
| JP | 2010-75235 A | 4/2010 |
| JP | 2010-75577 A | 4/2010 |
| JP | 2011-027986 A | 2/2011 |
| WO | WO 2011/140118 A1 | 11/2011 |

OTHER PUBLICATIONS

Japanese Office Action dated Mar. 24, 2015 from related Japanese Application No. 2015-501972, together with an English language translation.

International Search Report dated Jun. 17, 2014 issued in PCT/JP2014/062710.

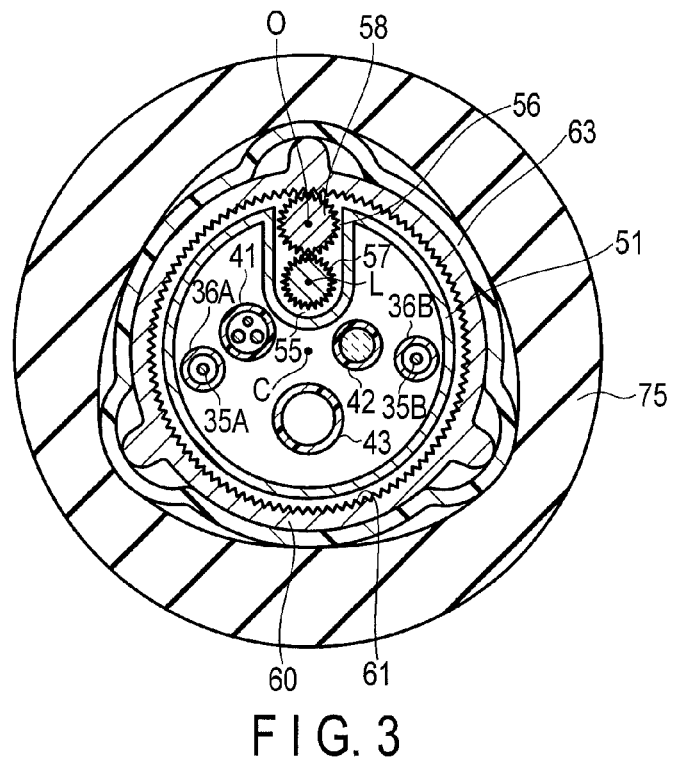
F I G. 3
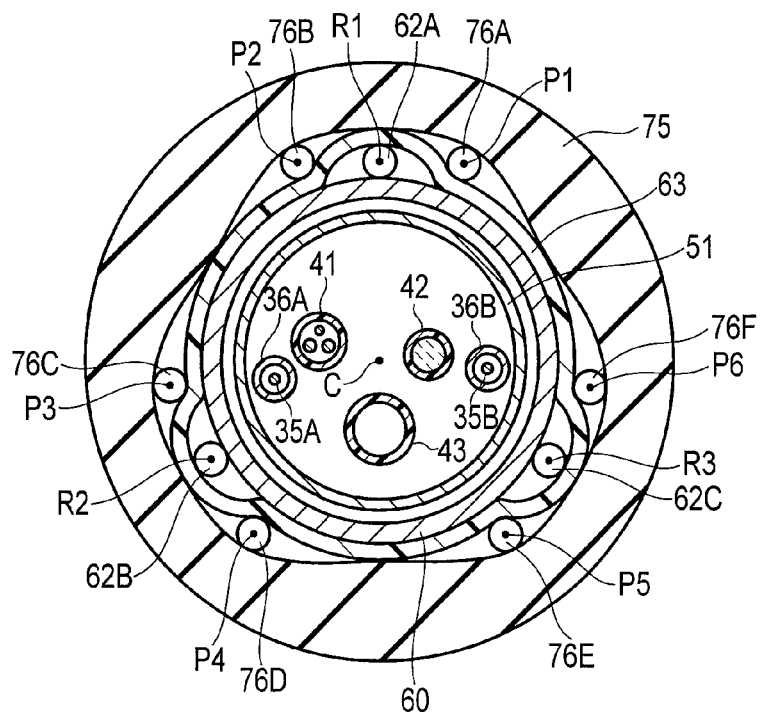
F I G. 4

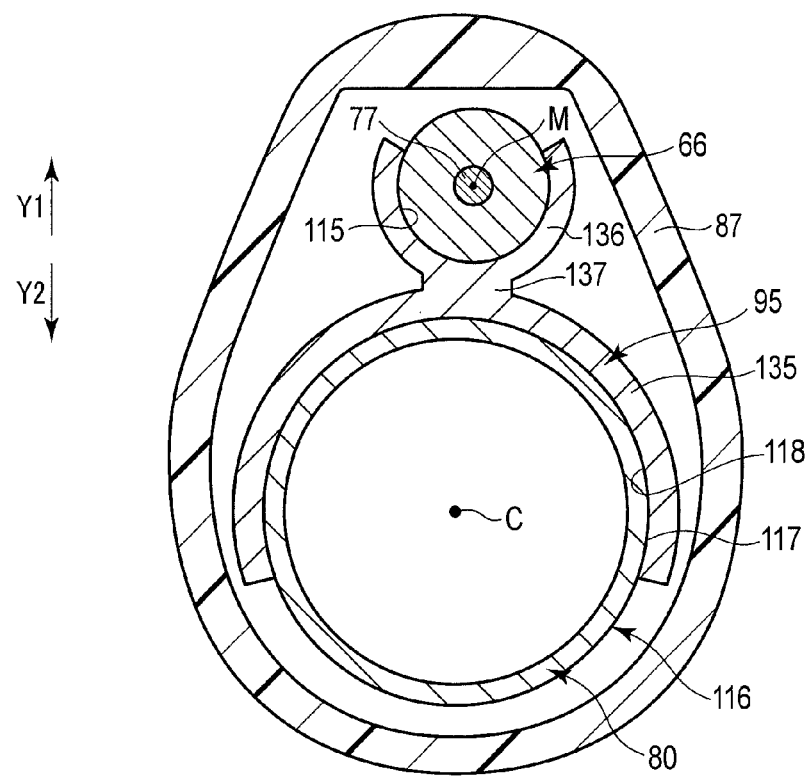
F I G. 10
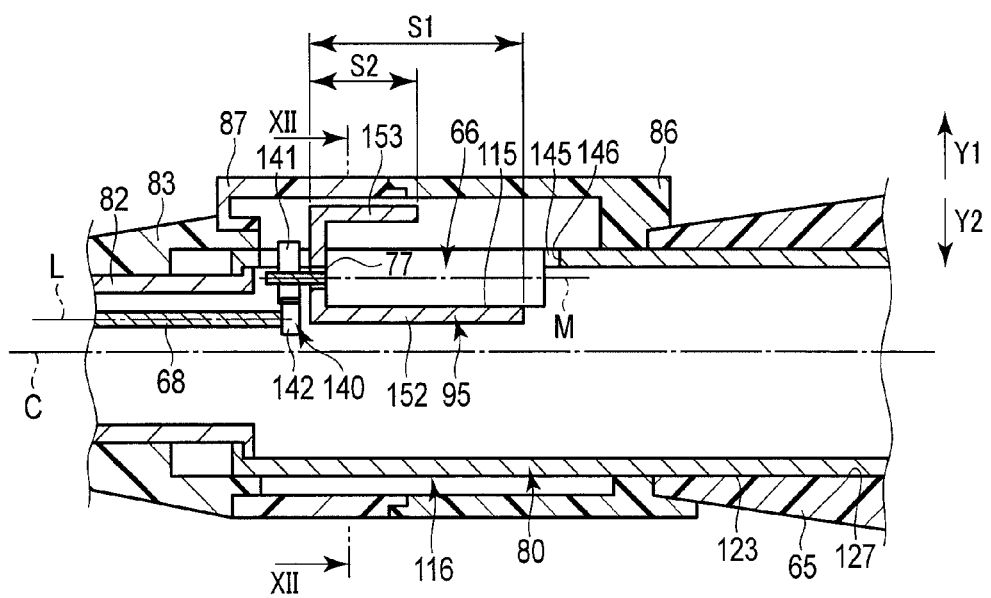
F I G. 11

INSERTION DEVICE

CROSS-REFERENCE TO RELATED APPLICATIONS

This is a Continuation Application of PCT Application No. PCT/JP2014/062710, filed May 13, 2014 and based upon and claiming the benefit of priority from prior Japanese Patent Application No. 2013-113936, filed May 30, 2013, the entire contents of which are incorporated herein by reference.

BACKGROUND OF THE INVENTION

1. Field of Invention

The present invention relates to an insertion device in which a movement portion moved by receiving a movement driving force is provided in an inserting section extending along a longitudinal axis or an attachment unit which is attached to the inserting section.

2. Description of Related Art

US 2012/0029281 discloses an endoscope device which is an insertion device, an attachment unit is attached to an inserting section extending along a longitudinal axis. The attachment unit includes a base tube to which the inserting section is inserted, and a fin which is spirally extended on an outer peripheral surface of the base tube. The attachment unit including the fin which is a movement portion rotates in one of directions around the longitudinal axis with respect to the inserting section when a movement driving force is transmitted. When the attachment unit including the fin rotates in a state that the fin is abutted to a lumen wall (lumen paries), etc., a propulsive force toward a distal direction or a propulsive force toward a proximal direction acts on the inserting section. In other words, when the fin motions in a state that a pressing force acts toward the inner peripheral direction, a propulsive force acts on the inserting section in one of the axis-parallel directions parallel to a longitudinal axis.

In this endoscope, an operation section is provided to the proximal side with respect to the inserting section. The operation section includes a grip held by an operator, and a member inserting section which opens to the outside. An electronic motor, which is a driving source for generating a movement driving force to rotate the fin (movement section), is attached to the member inserting section. In the inside of the inserting section, a driving shaft which is a line portion is extended along the longitudinal axis. Upon transmission of a movement driving force from the electric motor to the driving shaft, the driving shaft rotates about a line core axis. Upon rotation of the driving shaft, the movement driving force is transmitted to the fin via a base tube of the attachment unit, and the attachment unit rotates toward one of the directions around the longitudinal axis. The line core axis of the driving shaft is bent inside the operation section toward the member inserting section. Accordingly, between the bent position and the member inserting section, the line core axis is not parallel to the longitudinal axis.

BRIEF SUMMARY OF THE INVENTION

According to one aspect of the invention, an insertion device includes that: an inserting section which extends along a longitudinal axis; a movement section which is provided in the inserting section or an attachment unit which is attached to the inserting section, and which is configured to move to cause a propulsive force to act on the inserting section; a holdable grip which is provided to a proximal direction side with respect to the inserting section; a driving source which is configured to be driven so as to generate a movement driving force to move the movement section; a base member to which the grip is abutted; and a coupling member which includes a driving source-side abutting surface to which an outer peripheral surface of the driving source is abutted, and which couples the driving source to the base member.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 3 is a cross-sectional view taken along line III-III in FIG. 2.

FIG. 4 is a cross-sectional view taken along line IV-IV in FIG. 2.

FIG. 10 is a cross-sectional view taken along line X-X in FIG. 9.

FIG. 11 is a schematic cross-sectional view illustrating the structure between the grip and the second flexible tube section in the endoscope according to the second variation.

DETAILED DESCRIPTION OF THE INVENTION

First Embodiment

Figure 1:
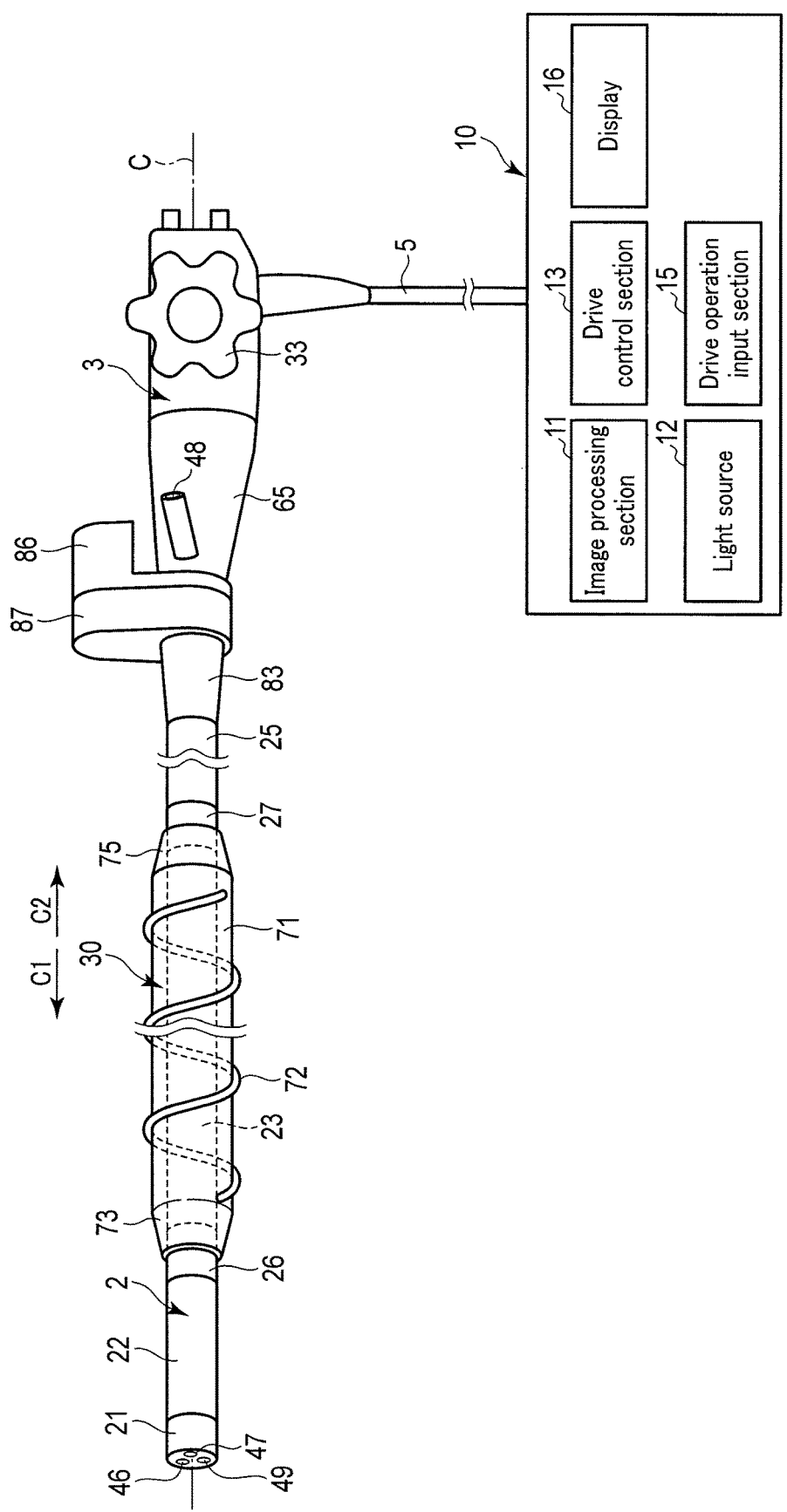
FIG. 1 is a schematic diagram of an endoscope according to the first embodiment of the present invention.

The first embodiment of the present invention will be explained with reference to FIG. 1 to FIG. 8. FIG. 1 shows an endoscope device 1 which is an inserting device according to the first embodiment. The endoscope device 1 has a longitudinal axis C as shown in FIG. 1. Directions parallel to the longitudinal axis C is defined as axis-parallel directions. One of the axis-parallel directions is defined as a distal direction (indicated by arrow C1 in FIG. 1), and direction opposite to the distal direction is defined as a proximal direction (indicated by arrow C2 in FIG. 1). The endoscope 1 includes an inserting section (an endoscope inserting section) 2 extending along the longitudinal axis C, and the operation section (an endoscopic operating section) provided to the proximal direction side with respect to the inserting section 2. The inserting section 2 is extended along the longitudinal axis C, and is inserted into a body cavity when the endoscope 1 is used.

One end of a universal cable 5 is connected to the operation section 3. The other end of the universal cable 5 is connected to a peripheral unit 10. The peripheral unit 10 includes an image processing section 11, such as an image processor, etc., a light source 12, a drive control section 13 which is a control device including a CPU (Central Processing Unit) and an ASIC (application specific integrated circuit), etc., a drive operation input section 15 having foot switches and buttons, etc., and a display 16, such as a monitor, etc.

The inserting section 2 includes a distal rigid section 21 forming a distal end of the inserting section 2, a bending section 22 provided to the proximal direction side with respect to the distal rigid section 21, and a first flexible tube section 23 provided to the proximal direction side with respect to the bending section 22, and a second flexible tube section 25 provided to the proximal direction side with respect to the first flexible tube 23. The bending section 22 and the first flexible tube section 23 are connected by a first relaying connecting section 26. The first flexible tube section 23 and the second flexible tube section 25 are connected by a second relaying connecting section 27.

An attachment unit 30 is provided to the outer peripheral side of the inserting section 2. The attachment unit 30 extends along the longitudinal axis C between the first relaying connecting section 26 and the second relaying connecting section 27. The attachment unit 30 is attached to the inserting section 2, while the inserting section 2 is inserted through the attachment unit 30. In the present embodiment, the attachment unit 30 is rotatable about the longitudinal axis with respect to the inserting section 2.

The attachment unit 30 includes a base tube 71 in a cylindrical shape, which is extended along the longitudinal axis C. A fin 72 is attached on the outer surface of the base tube 71. The fin 72 is spirally extended around the longitudinal axis C. A distal-side tapered portion 73 in a cylindrical shape is provided to the distal direction side of the base tube 71. The distal-side tapered portion 73 is formed in a tapered shape which diminishes in its outer diameter toward the distal direction side. A proximal-side tapered portion 75 in a cylindrical shape is provided to the proximal direction side of the base tube 71. The proximal-side tapered portion 75 is formed in a tapered shape which diminishes in its outer diameter toward the proximal direction side.

Figure 2:
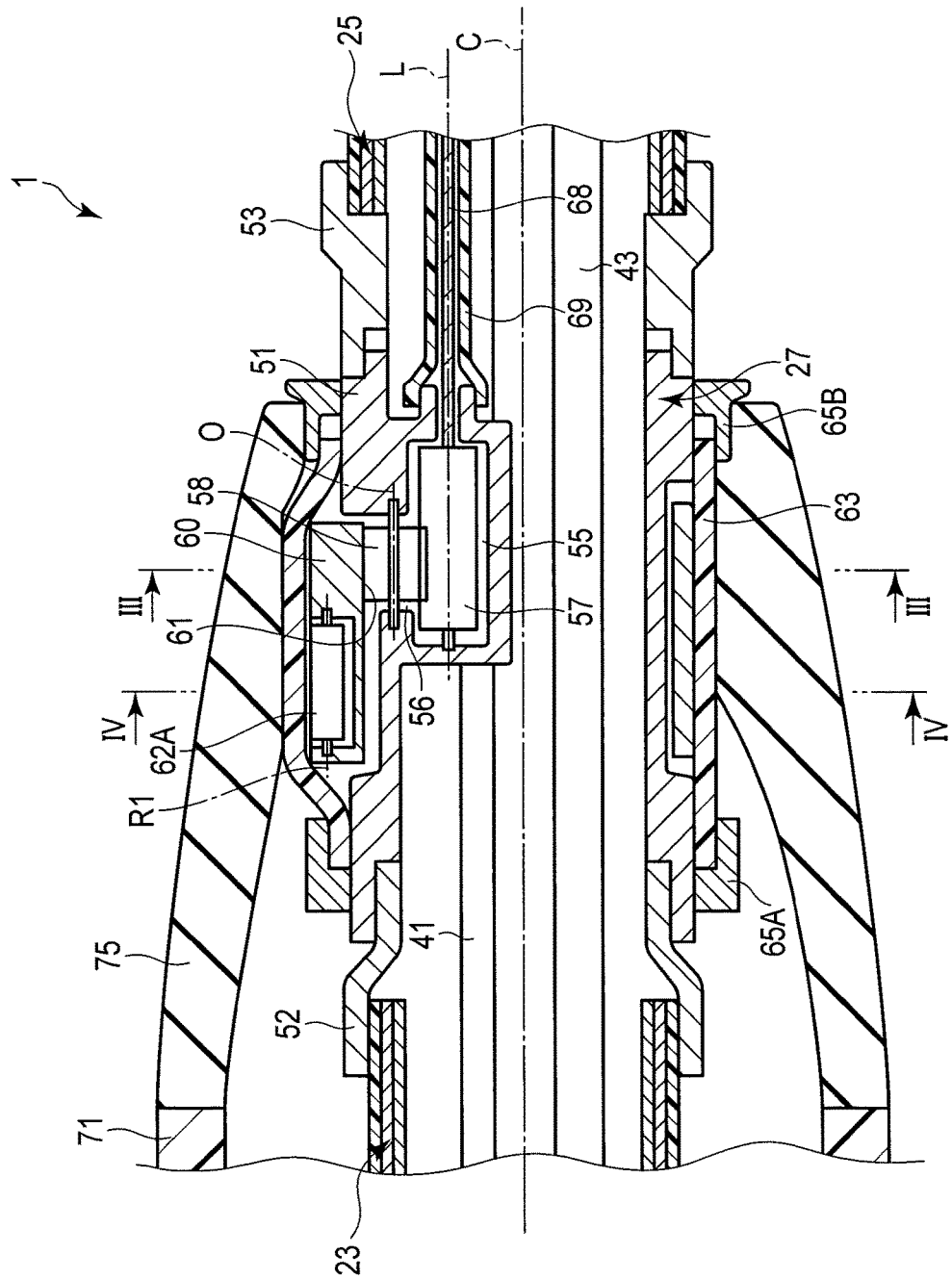
FIG. 2 is a schematic cross-sectional view illustrating the second relaying connecting section of the inserting section of the endoscope according to the first embodiment.

FIG. 2 shows the structure of the second relaying connecting section 27. FIG. 3 is a cross-sectional view taken along line in FIG. 2, and FIG. 4 is a cross-sectional view taken along line IV-IV in FIG. 2. As shown in FIG. 1, a bending operation knob 33, which serves as a bending operation input section to which a bending operation of the bending section 22 is input, is provided on the outer surface of the operation section 3. As shown in FIGS. 3 and 4, the bending wires 35A and 35B extend along the longitudinal axis C inside of the inserting section 2. The proximal ends of the bending wires 35A and 35B are connected to a pulley (not shown) coupled to the bending operation knob 33 inside the operation section 3. The distal ends of the bending wires 35A and 35B are connected to the distal portion of the bending section 22. Upon the bending operation at the bending operation knob 33, the bending wire 35A or 35B is pulled, and the bending section 22 is bent.

Each of the bending wires 35A and 35B is inserted through the corresponding coil 36A or 36B. The proximal ends of the coils 36A and 36B extend up to the inside of the operation section 3. The distal ends of the coils 36A and 36B are connected to the inner peripheral surface of the first relay connection section 26. In the present embodiment, the bending section 22 is bendable in two directions as the two bending wires 35A and 35B are provided. For example, the bending section 22 may be bendable in four directions if four bending wires are provided.

As shown in FIGS. 2 to 4, an imaging cable 41, a light guide 42, and a treatment tool channel tube 43 extend along the longitudinal axis C inside of the inserting section 2. An image sensor (not shown) configured to image an object is provided inside of the distal rigid section 21 (the distal portion of the inserting section 2). The image element performs imaging of an object through an observation window 46. The distal end of the imaging cable 41 is connected to the image sensor. The imaging cable 41 is extended through the inside of the inserting section 2, the inside of the operation section 3, and the inside of the universal cable 5, and the proximal end of the imaging cable 41 is connected to the image processing unit 11 of the peripheral unit 10. The obtained imaging of an object is processed by the image processing unit 11 to generate an image of the object. The generated image of the object is then displayed on the display 16.

The light guide 42 extends through the inside of the inserting section 2, the inside of the operation section 3, and the inside of the universal cable 5, and the proximal end of the lighting guide 42 is connected to the light source 12 of the peripheral unit 10. A light emitted from the light source 12 is guided by the light guide 42, and is irradiated on an object through a lighting window 47 of the tip portion (distal rigid section 21) of the inserting section 2.

As shown in FIG. 1, a treatment tool inserting section 48 to which a treatment tool, such as a forceps, etc., is inserted is provided on the outer surface of the operation section. The proximal end of the treatment tool channel tube 43 is connected to the treatment tool inserting section 48 through the inside of the inserting section 2 and the inside of the operation section 3. The treatment tool inserted from the treatment tool inserting section 48 projects from the opening 49 of the distal rigid section 21 toward the distal direction, through the inside of the treatment tool channel tube 43. Treatment is then performed with the treatment tool, while the treatment tool projects from the opening 49 of the distal rigid section 21.

As shown in FIG. 2, a supporting member 51 is provided in the second relaying connecting section 27. The proximal portion of the first flexible tube section 23 is coupled to the distal portion of the supporting member 51 through a relaying member 52. By that coupling, the first flexible tube section 23 and the second relaying connecting unit 27 are coupled. The distal portion of the second flexible tube section 25 is coupled to the proximal portion of the supporting member 51 through the relay member 53. By that coupling, the second flexible tube section 25 and the second relaying connecting unit 27 are coupled.

As shown in FIGS. 2 to 4, in the second relaying connecting section 27, a cavity 55 is formed by the supporting member 51. The cavity 55 opens toward the outer peripheral direction at an opening 56. A driving gear 57 and a relaying gear 58 are attached to the supporting member 51. The driving gear 57 is arranged in the cavity 55, and the relaying gear 58 is arranged in the proximity of the opening 56 of the cavity 55. The driving gear 57 engages with the relaying gear 58. The driving gear 57 is rotatable about the line core axis L, and the relaying gear 58 is rotatable about a gear axis O.

A rotating cylindrical member 60 is attached to the supporting member 51 of the second relaying connecting section 27. The rotating cylindrical member 60 is attached to the supporting member 51, while the inserting section 2 is inserted through the rotating cylindrical member 60. The rotating cylindrical member 60 is rotatable in directions around the longitudinal axis with respect to the inserting section 2 (the supporting member 51). An inner perimeter gear 61 is provided on the inner perimeter of the rotating cylindrical member 60 along all-round in the directions around the longitudinal axis. The inner perimeter gear 61 engages with the relaying gear 58.

In the present embodiment, three inner rollers 62A, 62B, and 62C are attached to the rotating cylindrical member 60. The inner rollers 62A, 62B, and 62C are approximately evenly spaced and placed in the directions around the longitudinal axis. Each of the inner rollers 62A, 62B, and 62C has a roller axis (R1, R2 or R3). The roller axes R1, R2, and R3 are extended approximately parallel with the longitudinal axis C. Each of the inner rollers 62A, 62B, and 62C is rotatable about the roller axis (R1, R2 or R3) with respect to the rotating cylindrical member 60. The inner rollers 62A, 62B, and 62C are rotatable integrally with the rotating cylindrical member 60 with respect to the inserting section 2 (the supporting member 51).

The rotating cylindrical member 60 and the inner rollers 62A, 62B, and 62C are covered by a cylindrical-shaped covering member 63 from the outer peripheral direction side. The distal end of the covering member 63 is fixed to the supporting member 51 via the stopping member 65A, and the proximal end of the covering member 63 is fixed to the supporting member 51 via the stopping member 65B. At a fixing position for the distal end of the covering member 63 and a fixing position for the proximal end of the covering member 63, the space between the supporting member 51 and the covering member 63 is liquid-tight. The structure can prevent liquid from flowing into the cavity 55, the rotating cylindrical member 60, and the inner rollers 62A, 62B, and 62C, which are located to the inner periphery direction side of the covering member 63. In the parts where the inner rollers 62A, 62B, and 62C are located in the directions around the longitudinal axis, the covering member 63 projects toward the outer periphery direction. The covering member 63 is fixed to the inserting section 2, and the rotating cylindrical member 60 is rotatable in directions around the longitudinal axis with respect to the covering portion 63.

As shown in FIG. 4, six outer rollers 76A through 76F are attached to the inner periphery surface of the proximal-side tapered portion 75. The outer rollers 76A to 76F are located to the outer periphery direction side of the covering member 63. In the directions around the longitudinal axis, the inner roller 62A is located between the outer roller 76A and the outer roller 76B, and the inner roller 62B is located between the outer roller 76C and the outer roller 76D. In the directions around the longitudinal axis, the inner roller 62C is located between the outer roller 76E and the outer roller 76F. Each of the outer rollers 76A to 76F has a roller axis (one of P1 to P6). Each of the outer rollers 76A to 76F is rotatable about the roller axis (one of P1 to P6) with respect to the covering member 63 and the proximal-side tapered portion 75. The outer rollers 76A to 76F are rotatable integrally with the attachment unit 30 with respect to the inserting section 2 (the supporting member 51). The roller axes P1 to P6 extend approximately parallel with the longitudinal axis C.

As shown in FIG. 2, the driving shaft 68 extends along the line core axis L inside of the second flexible tube section 25 of the inserting section 2. The distal end of the driving shaft 68 is connected to the driving gear 57. The distal end of the member channeling tube 69 is coupled to the supporting member 51. The driving shaft 68 extends inside the member channeling tube 69. The line core axis L of the driving shaft 68 is parallel to the longitudinal axis C. Thus, the driving shaft 68 is parallel to the longitudinal axis C from its distal end to its proximal end.

A movement driving force that rotates (i.e., moves) the fin 72 of the attachment unit 30 is transmitted through the driving shaft 68 which is a line portion. Upon transmission of an action driving force to the driving shaft 68, the driving shaft 68 rotates about the line core axis L toward one of directions around the line core axis L. As a result, the movement driving force is transmitted to the driving gear 57, and the driving gear 57 rotates about the line core axis L.

The rotation of the driving gear 57 causes the relaying gear 58 to rotate about the gear axis O, and the movement driving force is transmitted to the rotating cylindrical member 60 via the relaying gear 58. As a result, the rotating cylindrical member 60 rotates toward one of the directions around the longitudinal axis, and the inner rollers 62A through 62C move in one of the directions around the longitudinal axis with respect to the inserting section 2 and the covering member 63.

When the rotating cylindrical member 60 rotates, the inner roller 62A presses on the outer roller 76A or the outer roller 76B. Similarly, the inner roller 62B presses on the outer roller 76C or the outer roller 76D, and the inner roller 62C presses on the outer roller 76E or the outer roller 76F. Thus, the action driving force is transmitted from the inner rollers 62A through 62C to the attachment unit 30 including the proximal-side tapered portion 75 and the base tube 71, and the attachment unit 30 rotates toward one of the directions around the longitudinal axis with respect to the inserting section 2 and the covering member 63. In other words, the movement driving force is transmitted to the fin 72 attached to the base tube 71, and the fin 72, which serves as a movement section, rotates (moves) in directions around the longitudinal axis.

It should be noted that friction between each of the inner rollers 62A, 62B, and 62C and the covering member 63 will be reduced because each of the inner rollers rotates about the roller axis (R1, R2 or R3). Similarly, it should be noted that friction between each of the outer rollers 76A through 76F and the covering member 63 will be reduced because each of the inner rollers rotates about the roller axis (one of P1 to P6). Thus, the movement driving force is properly transmitted from the inner rollers 62A through 62C to the attachment unit 30, and the attachment unit 30 can properly rotate.

When the attachment unit 30 (fin 72) rotates in a state that a wall portion, such as a lumen wall, etc., is abutted to the fin 72, a propulsive force toward a distal direction or toward a proximal direction acts on the inserting section 2. In other words, if the fin 72 is motioned while a pressing force is being applied to the fin 72, which serves as a movement section toward the inner periphery direction side, the propulsive force acts on the inserting section 2 toward one of the axis-parallel directions parallel to the longitudinal axis C. The propulsive force can improve ease of insertion and extraction of the inserting section 2 in a lumen.

As shown in FIG. 1, a grip 65 to be held by an operator when using the endoscope device 1 is provided to the operation section 3. The grip 65 is made of a resin material, and constitutes a part of the exterior of the operation section 3. The grip 65 is located to the distal direction side with respect to the bending operation knob 33.

Figure 5:
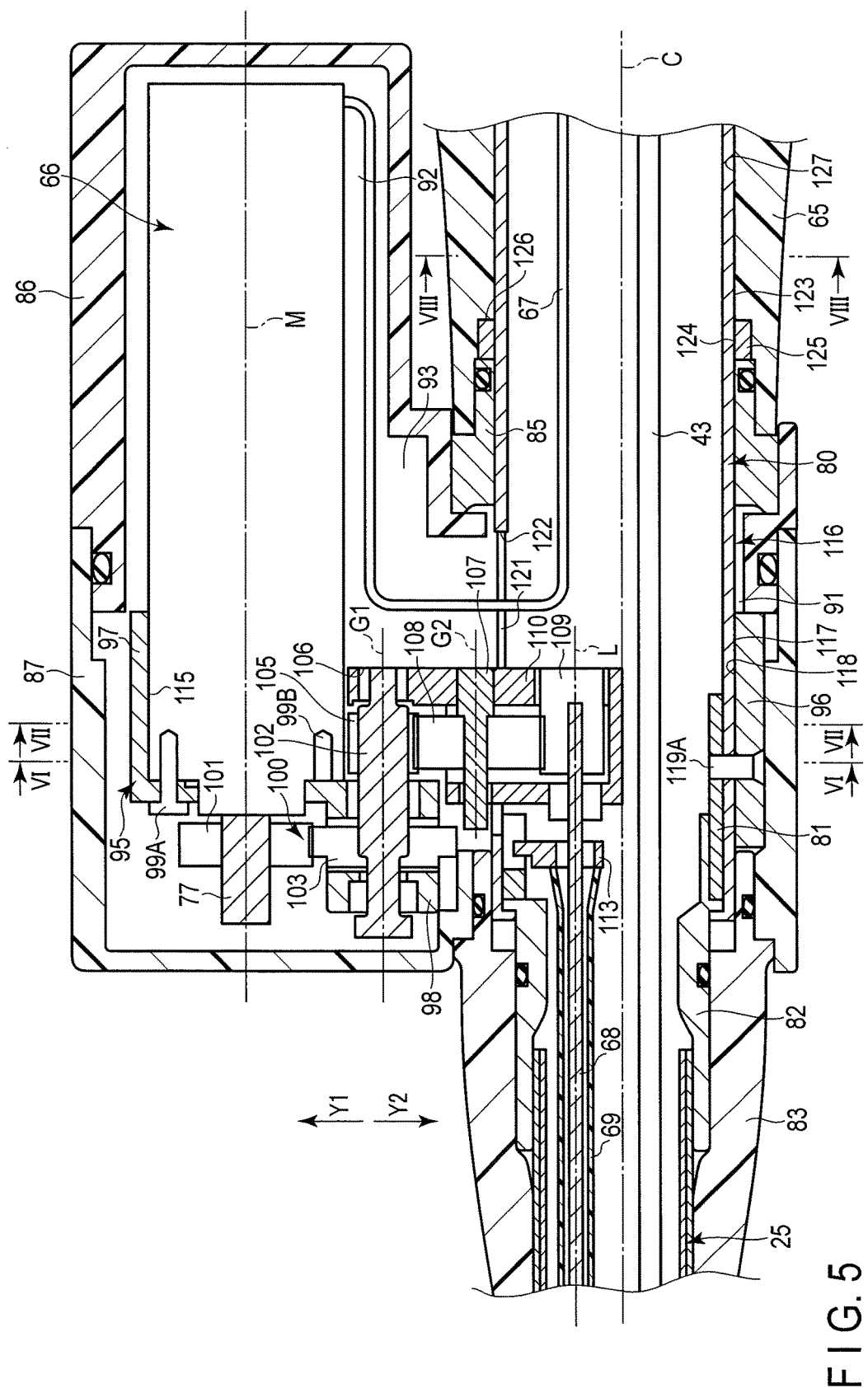
FIG. 5 is a schematic cross-sectional view illustrating the structure between the grip and the second flexible tube section in the endoscope according to the first embodiment.
Figure 6:
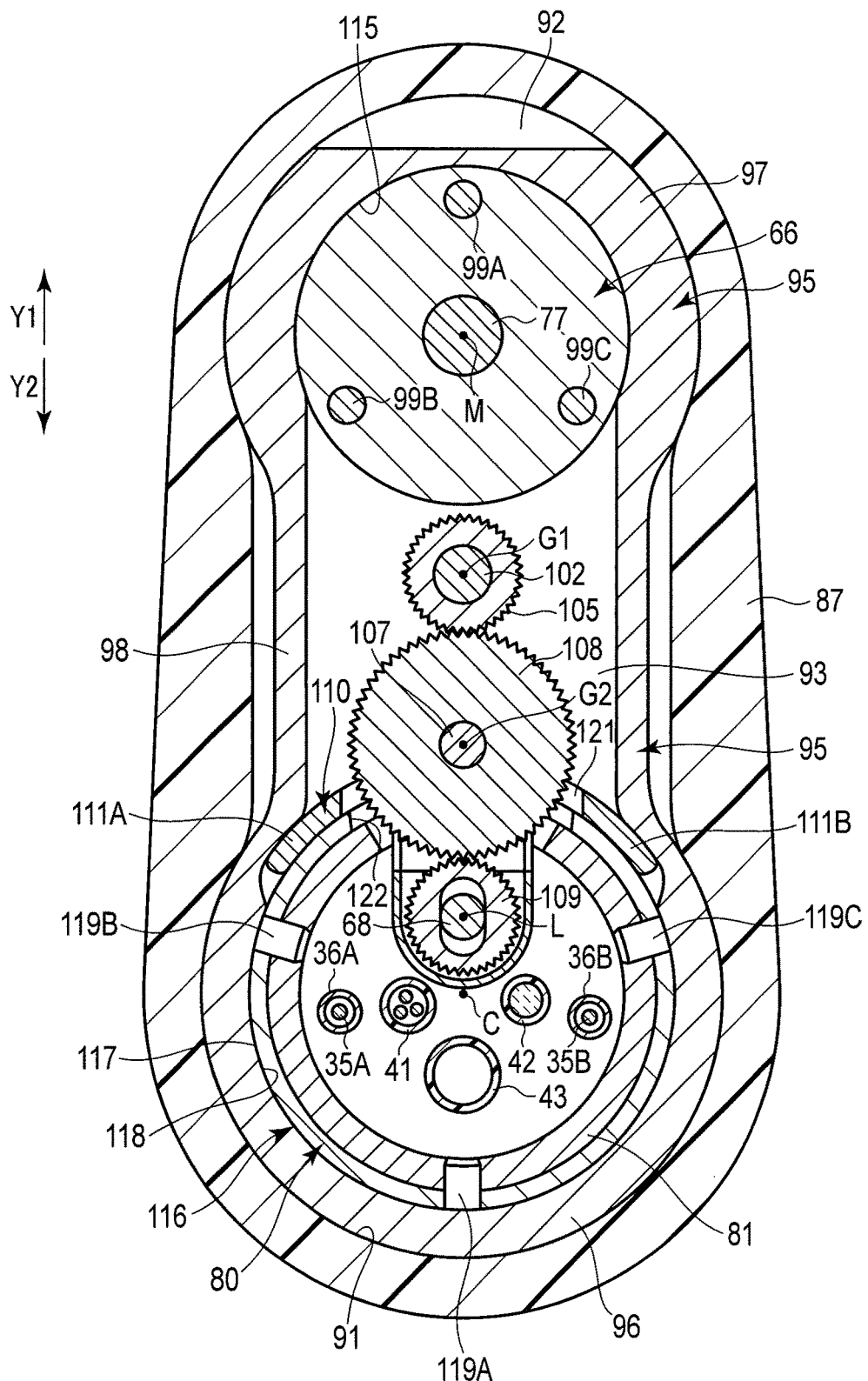
FIG. 6 is a cross-sectional view taken along line VI-VI in FIG. 5.
Figure 7:
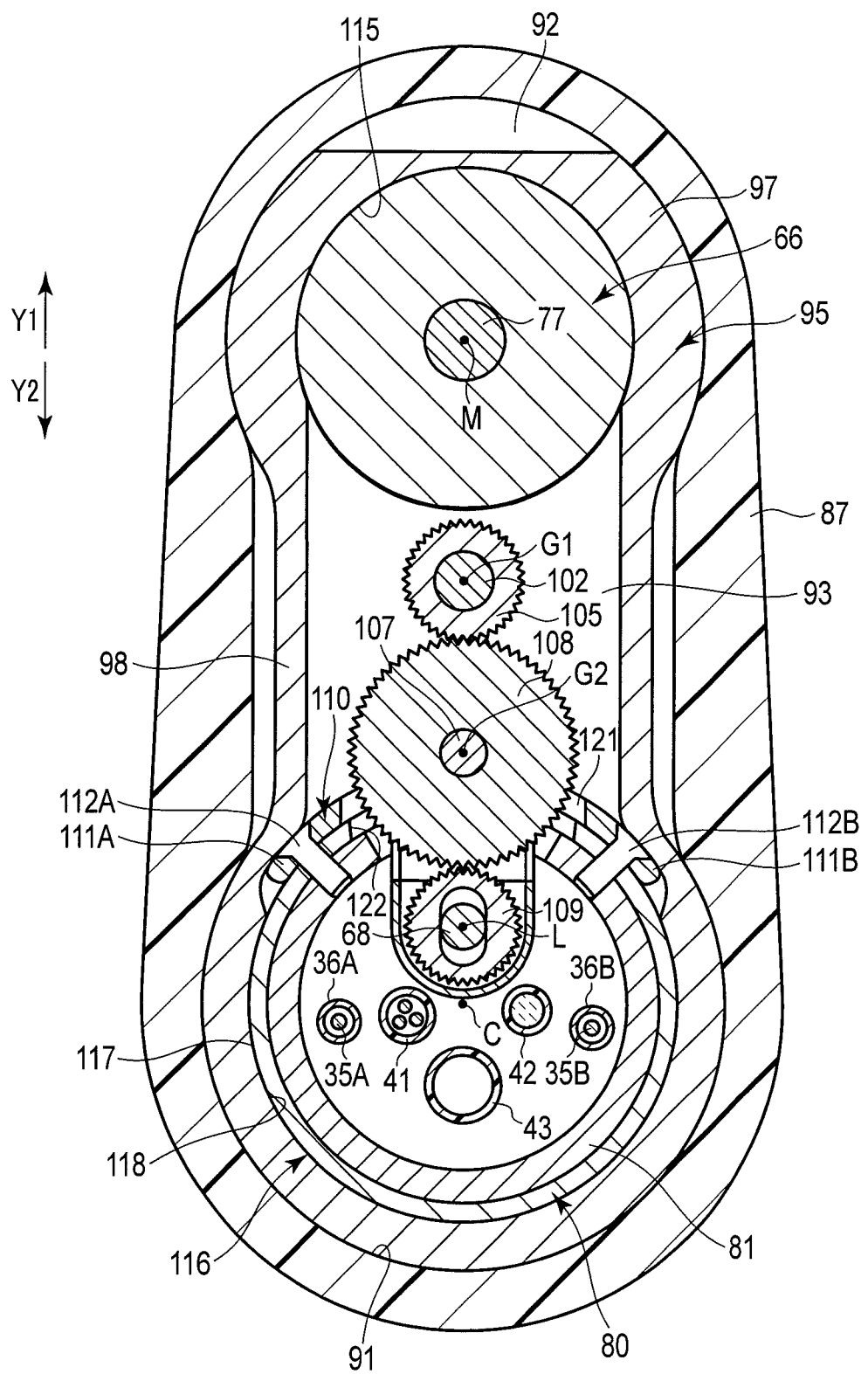
FIG. 7 is a cross-sectional view taken along line VII-VII in FIG. 5.
Figure 8:
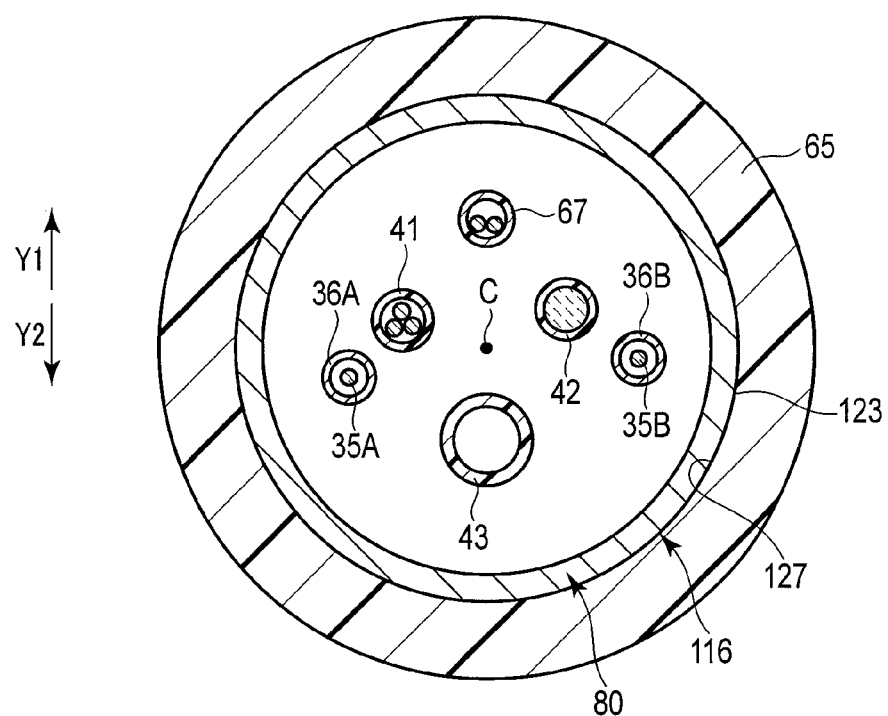
FIG. 8 is a cross-sectional view taken along line VIII-VIII in FIG. 5.

FIG. 5 shows the structure between the grip 65 and the second flexible tube section 25. FIG. 6 is a cross-sectional view taken along line VI-VI in FIG. 5, FIG. 7 is a cross-sectional view taken along line VII-VII in FIG. 5, FIG. 8 is a cross-sectional view taken along line VIII-VIII in FIG. 5. As shown in FIGS. 5 through 8, a cylindrical-shaped base member 80 is provided between the second flexible tube section 25 and the grip 65. The base member 80 extends along the longitudinal axis C with the longitudinal axis C being an axial center. The base member 80 is made of materials having a high vibration transmissibility, e.g., metals, etc. The inserting section 2 is located to the distal direction side with respect to the base member 80.

A cylindrical member 81 is coupled to the base member 80. The distal portion of the base member 80 is located to the outer periphery direction side of the cylindrical member 81. The distal portion of the base member 80 and the cylindrical member 81 are coupled to the proximal portion of the second flexible tube section 25 through the cylindrical-shaped connecting member 82. A cylindrical-shaped break prevention member 83 covers the proximal portion of the second flexible tube section 25. The proximal portion of the break prevention member 83 is coupled to the connecting member 82 and the distal portion of the base member 80.

A proximal-side case 86 is coupled to the base member 80 via a connecting ring 85. A distal-side case 87 is coupled to the distal direction side of the proximal-side case 86. Herein, one of the directions perpendicular to the longitudinal axis C is defined as a first perpendicular direction (indicated by arrow Y1 in FIGS. 5 to 8), and the direction opposite to the first perpendicular direction is defined as a second perpendicular direction (indicated by arrow Y2 in FIGS. 5 to 8). A base-located cavity 91 extending along the longitudinal axis C, a motor housing cavity 92 located to the first perpendicular direction side with respect to the base-located cavity 91, and a relaying cavity 92 provided between the base-located cavity 91 and the motor housing cavity 92 are formed inside the proximal-side case 86 and the distal-side case 87.

A coupling member 95 is provided inside the proximal-side case 86 and the distal-side case 87. The coupling member 95 is made of materials having a high vibration transmissibility, e.g., metals, etc. The coupling member 95 includes a base fixing portion 96 located in the base-located cavity 91, a driving source attaching portion 97 located in the motor housing cavity 92, and a relay continuing portion 98 which is continuous between the base fixing portion 96 and the driving source attaching portion 97.

An electric motor 66 which is a driving source is attached to the driving source attaching portion 97 of the coupling member 95 by connecting screws 99A to 99C. The electric motor 66 is attached to the driving source attaching portion 97; the electric motor 66 is therefore located to the first perpendicular direction side with respect to the longitudinal axis C. Furthermore, in the present embodiment, the electric motor 66 is attached to the driving source attaching portion 97; the electric motor 66 is therefore located outside of the base member 80. One end of a motor cable 67 is connected to the electric motor 66. The motor cable 67 extends through the inside of the base member 80, the inside of the operation section 3, and the inside of the universal cable 5, and the other end of the cable is coupled to the drive control section 13 of the peripheral unit 10. In the present embodiment, the proximal end of the coupling member 95 is located to the distal direction side of the proximal end of the electric motor 66.

By an operation input by the drive operation input section 15, the drive control section 13 supplies an electric power to the electric motor 66 via the motor cable 66 to drive the electric motor 66. The electric motor 66 includes a motor shaft 77 that rotates about the drive axis M when the electric motor 66 is driven. A movement driving force that rotates (i.e., motions) the attachment unit 30 (fin 72) is caused by rotating the motor shaft 77. The drive axis M of the electric motor 66 is parallel to the longitudinal axis C.

A relaying gear 101 is attached to the motor shaft 77. The relaying gear 101 is rotatable about the drive axis M integrally with the motor shaft 77. A relaying gear (driving source-side gear) 103 is attached to the coupling member 95 via a shaft member 102. The shaft member 102 and the relaying gear 103 are integrally rotatable about a gear axis G1. The relaying gear 103 engages with the relaying gear 101. The relaying gear 103 is located to the second perpendicular direction side with respect to the electric motor 66 and the relaying gear 101. The gear axis G1 is parallel to the drive axis M of the electric motor 66 and the longitudinal axis C.

A block body 110 is attached to the base member 80. The block body 110 includes engagement claws 111A and 111B located between the coupling member 95 and the base member 810 in the base-located cavity 91. Each of the engagement claws 111A and 111B is fixed to the base member 80 by a corresponding fixing screw 112A or 112B. Thus, the block body 110 is attached to the base member 80.

A relaying gear (base-side gear) 105 is attached to the block body 110. A shaft engaging portion 106, with which the shaft member 102 engages, is provided in the block body 110. By engaging the shaft member 102 inserted through the relaying gear 105 with the shaft engaging portion 106, the coupling member 95 is coupled to the block body 110. When the coupling member 95 is coupled to the block body 110, the relaying gear 105 shares the same axis with the shaft member 102 and the relaying gear 103. Accordingly, when the coupling member 95 is coupled to the block body 110, the relaying gear (base-side gear) 105 rotates about the gear axis G1 which is coaxial with the shaft member 102 and the relaying gear (driving source-side gear) 103.

A relaying gear 108 is attached to the block body 110 via the shaft member 107. The shaft member 107 and the relaying gear 108 are integrally rotatable about a gear axis G2. The relaying gear 108 engages with the relaying gear 105. The relaying gear 108 is located to the second perpendicular direction side with respect to the shaft member 102 and the relaying gear 105. The gear axis G2 is parallel to the drive axis M of the electric motor 66 and the longitudinal axis C.

A relaying gear 109 is attached to the block body 110. The relaying gear 109 engages with the relaying gear 108. The relaying gear 109 is located to the second perpendicular direction side with respect to the relaying gear 108. The proximal end of the driving shaft 68 is connected to the relaying gear 109. The relaying gear 109 is arranged so as to share the same axis with the driving shaft 68. Thus, the relaying gear 109 is rotatable about the line core axis L which is parallel to the longitudinal axis C integrally with the driving shaft 68 which is a strand portion. The proximal end of the member channeling tube 69 is connected to the cylindrical member 81 via the connecting member 113.

A movement driving force generated by driving the driving motor 66 is transmitted to the relaying gear 103 via the relaying gear 101. Thus, the shaft member 102 rotates about the gear axis G2 integrally with the relaying gear (driving source-side gear) 103 and the relaying gear (block-side gear) 102. The action driving force is then transmitted to the driving shaft 68 via the relaying gear 108, the shaft member 107, and the relaying gear 109. As stated above, the relaying gears 101, 103, 105, 108, 109, and the shaft members 102 and 107 constitute a driving force transmitting section 100 which is configured to transmit a movement driving force generated in the electric motor 66 (driving source) to the driving shaft 68 (line portion). The movement driving force transmitted to the driving shaft 68 is transmitted to the attachment unit 30 (fin 72) as described above, and the fin then rotates (i.e., moves).

A driving source-side abutting surface (abutting surface) 115, to which the electric motor 66 which is a driving source is abutted, is provided in the driving source attaching portion 97 of the coupling member 95. A part of the inner periphery of the driving source attaching portion 97 constitutes the driving source-side abutting surface 115. In the cross section perpendicular to the longitudinal axis C, the driving source-side abutting surface 115 is formed in the shape of an arc around the drive axis M of the electric motor 66. The electric motor 66 is abutted to the driving source-side abutting surface 115 covering the range of 180 degrees or more in directions around the drive axis. In the present embodiment, only the distal-direction-side part of the electric motor 66 in the axis parallel directions that are parallel to the longitudinal axis C is abutted to the driving source-side abutting surface 115.

When the fin 72 which serves as an action section rotates, the fin 72 sometimes fails to rotate properly because of a load coming from a wall portion such as a lumen wall. In this case, the load against the fin 72 will increase, and the increased load will be transmitted to the motor shaft 77 of the electric motor 66, which is a driving source, via the driving shaft 68 and the driving force transmitting section 100. The driving status of the electric motor 66 is controlled by current control based on a control property which is set in advance by the drive control section 13. When the load against the fin 72 is small, the driving status of the electric motor 66 is controlled by the control property that has been set. However, when the increased load is transmitted to the electric motor 66, disturbance will occur in the control of the driving status of the electric motor 66. While disturbance occurs, a driving torque that drives the electric motor 66 is increased, and thus the excessively large electric power will be supplied to the electric motor 66 in order to forcefully drive the electric motor 66 with the increased driving torque. Accordingly, when disturbance occurs, the control property which was set in advance will be changed in controlling the driving status of the electric motor 66. As the preset control property is changed to another, the electric motor 66 starts to vibrate. The more load against the fin 72 increases, the more the electric motor 66 vibrates. The vibration generated in the electric motor 66 is then transmitted to the driving source-side abutting surface 115 to which the electric motor 66 is abutted.

The base member 80 includes an arc-shaped outer peripheral surface (outer peripheral surface) 116 which is formed in a shape of a segment of a circle around the longitudinal axis C in the cross section perpendicular to the longitudinal axis C. The arc-shaped outer peripheral surface 116 extends along the longitudinal axis C. A vibration receiving surface 117 is provided on the distal portion of the arc-shaped outer peripheral surface 116. The vibration receiving surface 117 constitutes a part of the arc-shaped outer peripheral surface 116, and thus, it is formed in the shape of a segment of a circle around the longitudinal axis C in the cross section perpendicular to the longitudinal axis C.

A base-side abutting surface (abutting surface) 118, formed in an arc shape corresponding to the vibration receiving surface 117 in the cross section perpendicular to the longitudinal axis C, is provided in the base fixing portion 96 of the coupling member 95. A part of the inner periphery of the base fixing portion 96 constitutes the base-side abutting surface 118. The base-side abutting surface 118 is fixed to the base member 80 and the cylindrical member 81 with the fixing screws 119A through 119C. The base-side abutting surface 118 abuts to the vibration receiving surface 117 from the outer periphery direction side. The base-side abutting surface 118 is abutted to the vibration receiving surface 117 covering the range of 180 degrees or more in directions around the longitudinal axis. Thus, the electric motor 66 and the base member 80 are coupled by the coupling member 95.

Since the coupling member 95 is made of a material having a high vibration transmissibility, such as metals, etc., the vibration transmitted from the electric motor 66 to the driving source-side abutting surface 115 is transmitted to the base-side abutting surface 118. The vibration is then transmitted to the vibration receiving surface 117 of the base member 80 to which the base-side abutting surface 118 of the coupling member 95 is abutted.

An opening-defining surface 122 is provided at the base member 80 and the cylindrical member 81. The opening-defining surface 122 defines an opening 121 which opens toward the outside of the base member 80. The opening 121 opens toward the first perpendicular direction. The block body 110 and the relaying gear 109 are inserted in the inside of the cylindrical member 81 (i.e., the inside of the base member 80) from the opening 121. The relaying gear 109 engages with the relaying gear 108 in the proximity of the opening 121.

A vibration transmitting surface 123 is provided on the arc-shaped outer peripheral surface 116 of the base member 80. The vibration transmitting surface 123 is located to the proximal direction side with respect to the vibration receiving surface 117. Since the vibration transmitting surface 123 constitutes a part of the arc-shaped outer peripheral surface 116, the vibration transmitting surface 123 is formed in the shape of a segment of a circle around the longitudinal axis C in the cross section perpendicular to the longitudinal axis C. Since the base member 80 is made of a material having a high vibration transmissibility, such as a metal, etc., the vibration transmitted from the coupling member 95 to the vibration receiving surface 117 is transmitted to the vibration transmitting surface 123. In other words, the vibration is transmitted toward the proximal direction in the base member 80.

The grip 65 is attached to the base member 80 from the proximal direction side via a G ring 125. The G ring 125 is fixed to the base member 80 in a manner such that the inner peripheral surface is pressured-contact to the outer peripheral surface of the base member 80. The grip 65 is abutted to the proximal-side end face 126 of the G ring 125 fixed to the base member 80 in a manner such that the grip 65 is pressured-contact to the end face 126. The grip 65 extends along the longitudinal axis C. An inner peripheral abutting surface (abutting surface) 127, formed in an arc shape corresponding to the vibration transmitting surface 123 in the cross section perpendicular to the longitudinal axis C, is provided in the grip 65. A part of the inner periphery of the grip 65 constitutes the inner peripheral abutting surface 127. The inner peripheral abutting surface 127 is abutted to the vibration transmitting surface 123 from the outer peripheral direction side. The inner peripheral abutting surface 127 is abutted to the vibration transmitting surface 123 around the entire periphery in directions around the longitudinal axis.

The vibration transmitted to the base member 80 is transmitted to the G ring 125 via the inner peripheral surface 124. The vibration transmitted to the G ring 125 is then transmitted to the grip 65 via the proximal-side end face 126. The vibration transmitted to the vibration transmitting surface 123 of the base member 80 is transmitted to the inner peripheral abutting surface 127 abutted to the vibration transmitting surface 123. Thus, the vibration generated at the electric motor 66, which is a driving source, is transmitted to the grip 65. The outer peripheral surface of the grip 65 extends in a manner such that the first-perpendicular-direction-side part thereof has a gap from the proximal-side case 86.

Next, the function and advantageous effects of the endoscope device 1, which is an insertion device, is described. When using the endoscope device 1, the inserting section 2 is inserted into, for example, a lumen while the attachment unit 30 is attached to the inserting section 2. The electric motor 66 is driven while the fin 72 is abutted to a lumen wall, and the fin 72 rotates toward one of the directions around the longitudinal axis with respect to the inserting section 2, as described above. If the fin 72 rotates (that is moves) while a pressing force is being applied toward the inner periphery direction to the fin 72 which serves as a movement section, the propulsive force acts on the inserting section 2 in one of the axis-parallel directions parallel to the longitudinal axis C. Ease of insertion of the inserting section 2 in the lumen is improved by the propulsive force toward the distal direction, and ease of extraction of the inserting section 2 in the lumen is improved by the propulsive force toward the proximal direction.

When the fin 72 which serves as an action section rotates, the fin 72 sometimes fails to rotate properly because of a load coming from a wall portion such as a lumen wall. In this case, the load against the fin 72 will increase, and the increased load will be transmitted to the motor shaft 77 of the electric motor 66, which is a driving source, via the driving shaft 68 and the driving force transmitting section 100. The driving status of the electric motor 66 is controlled by current control based on the control property which is set in advance by the drive control section 13. When the load against the fin 72 is small, the driving status of the electric motor 66 is controlled by the control property that has been set. However, when the increased load is transmitted to the electric motor 66, disturbance will occur in the control of the driving status of the electric motor 66. While disturbance occurs, the driving torque that drives the electric motor 66 is increased, and thus the excessively large electric power will be supplied to the electric motor 66 in order to forcefully drive the electric motor 66 with the increased driving torque. Accordingly, when disturbance occurs, the control property which was set in advance will be changed in the control of the driving status of the electric motor 66. As the preset control property is changed to another, the electric motor 66 starts to vibrate. Herein, the line core axis L of the driving shaft 68 is parallel to the longitudinal axis C, and the driving shaft 68 is parallel to the longitudinal axis C from the distal end to the proximal end. Thus, the driving shaft 68 is not bent between the driving gear 57 and the relaying gear 109. Since the driving shaft 68 is not bent, a load, etc. due to a bend of the driving shaft 68 will not be transmitted to the electric motor 66 which is a driving source. In other words, a load other than the loads acted against the fin 72 is effectively prevented from being transmitted to the electric motor 66. Thus, it is possible to prevent vibration of the electric motor 66 due to loads, except for the load acted on the fin 72.

The vibration generated in the electric motor 66 is then transmitted to the driving source-side abutting surface 115 of the coupling member 95. The vibration is then transmitted from the driving source-side abutting surface 115 to the base-side abutting surface 118 through the coupling member 95, and then from the base-side abutting surface 118 to the vibration receiving surface 117 of the base member 80. The vibration is then transmitted from the vibration receiving surface 117 to the vibration transmitting surface 123 in the base member 80. The vibration is transmitted from the outer peripheral surface of the base member 80 to the inner peripheral surface 124 of the G ring 125, and then transmitted from the inner peripheral surface 124 to the proximal-side end face 126 through the G ring 125. The vibration is then transmitted to the grip 65 via the proximal-side end face 126. The vibration transmitted to the base member 80 is transmitted froth the vibration transmitting surface 123 to the inner peripheral abutting surface 127 of the grip 65. Thus, as described above, the vibration generated in the electric motor 66 is transmitted to the grip 65. Herein, the coupling member 95 and the base member 80 are made of materials having a high vibration transmissibility, e.g., metals, etc. Thus, the vibration generated at the electric motor 66 can be properly transmitted to the grip 65.

The operator holds the grip 65 with their hand when using the endoscope device 1. Since the vibration is transmitted to the grip 65, the vibration can be sensed properly by the operator's hand. With the above-described configuration, the vibration of the electric motor 66 due to loads, except for the load acted on the fin 72, can be effectively prevented. Thus, when the operator senses the vibration of the grip 65, the operator can properly recognize the load-acting status in which the load acts on the fin 72.

The vibration transmitting surface 123, which is formed in a shape of an arc around the longitudinal axis C in the cross section perpendicular to the longitudinal axis C, is provided in the base member 80. The inner peripheral abutting surface 127, formed in an arc shape corresponding to the vibration transmitting surface 123 in the cross section perpendicular to the longitudinal axis C, is directly abutted to the vibration transmitting surface 123 from the outer peripheral direction side, without involving any member. Thus, transmissibility of vibration from the base member 80 to the grip 65 can be ensured. As a result, transmissibility of the vibration generated in the electric motor 66 to the grip 65 is further improved. Furthermore, transmissibility of the vibration from the base member 80 to the grip 65 is further improved by abutting the inner peripheral abutting surface 127 to the vibration transmitting surface 123 around the entire periphery in directions around the longitudinal axis.

The vibration receiving surface 117, which is formed in a shape of an arc around the longitudinal axis C in the cross section perpendicular to the longitudinal axis C, is provided in the base member 80. The base-side abutting surface 118, formed in an arc shape corresponding to the vibration receiving surface 117 in the cross section perpendicular to the longitudinal axis C, is directly abutted to the vibration receiving surface 117 from the outer peripheral direction side, without involving any member. Thus, transmissibility of vibration from the coupling member 95 to the base member 80 can be ensured. As a result, transmissibility of the vibration generated in the electric motor 66 to the grip 65 is further improved. Furthermore, the transmissibility of the vibration from the coupling member 95 to the base member 80 is further improved by abutting the base-side abutting surface 118 to the vibration receiving surface 117 covering the range of 180 degrees or more in the directions around the longitudinal axis.

The driving source-side abutting surface 115, which is formed in a shape of an arc around the drive axis M of the electric motor 66 in the cross section perpendicular to the longitudinal axis C, is provided to the coupling member 95. The electric motor 66 is abutted to the driving source-side abutting surface 115 covering the range of 180 degrees or more in the directions around the driving axis. Thus, transmissibility of vibration from the electric motor 66 to the coupling member 95 can be ensured. As a result, transmissibility of the vibration generated in the electric motor 66 to the grip 65 is further improved.

The driving force transmitting section 100, configured to transmit the movement driving force generated in the electric motor 66 to the driving shaft 68, is formed by coupling the block body 110 to the coupling member 95. The relaying gear (driving source-side gear) 103 is attached to the coupling member 95 via the shaft member 102, and the relaying gear (base-side gear) 105 is attached to the block body 110. When the block body 110 is coupled to the coupling member 95, the relaying gear (base-side gear) 105 is arranged so as to be coaxial with the shaft member 102 and the relaying gear (driving source-side gear) 103, and the shaft member 102 is engaged with the shaft engaging portion 106 which is provided in the block body 110. Thus, the relaying gear (base-side gear) 105 becomes rotatable about the gear axis G1 integrally with the shaft member 102 and the relaying gear (driving source-side gear) 103, and the driving force transmitting section 100 is formed. The above-described configuration facilitates the coupling of the block body 110 to the coupling member 95 and the constituting of the driving force transmitting section 100.

(Examples of Variations)

Figure 9:
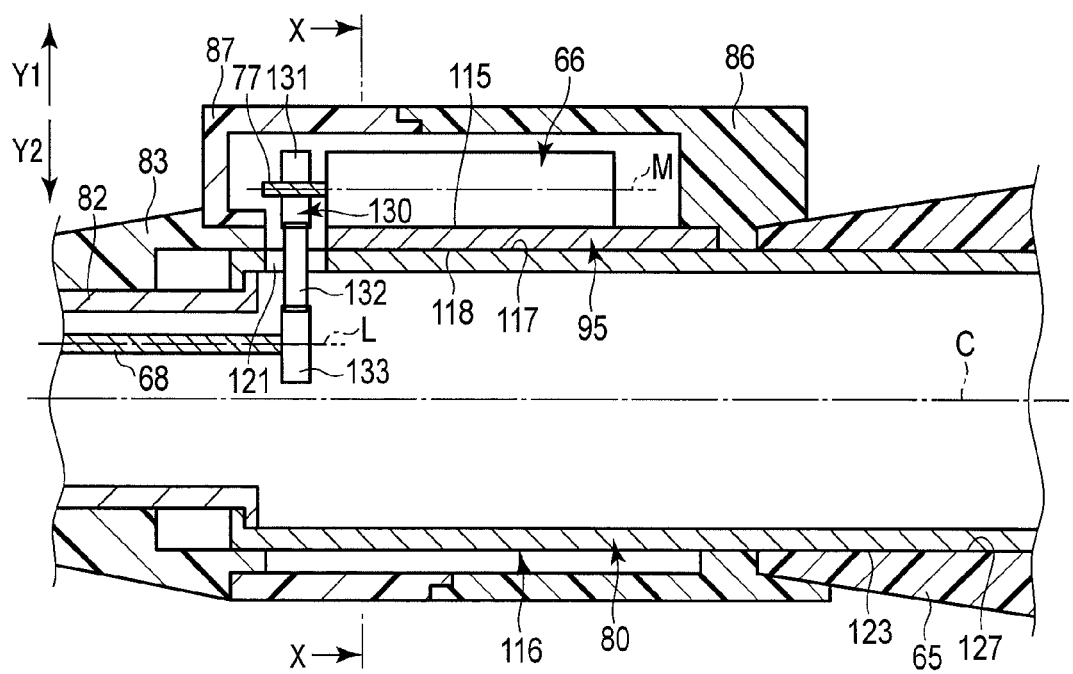
FIG. 9 is a schematic cross-sectional view illustrating the structure between the grip and the second flexible tube section in the endoscope according to the first variation.

In the first embodiment, the proximal end of the coupling member 95 is located to the distal direction side with respect to the proximal end of the electric motor 66; however, the location is not limited thereto. For example, in the first example of a variation which will be described below as shown in FIGS. 9 and 10, the coupling member 95 may extend up to a part located to the proximal direction side from the proximal end of the electric motor 66. Herein, in the examples shown in FIGS. 9 and 10, only the elements essential for the structure for transmitting a movement driving force from the electric motor 66 to the driving shaft 68 and the structure for transmitting the vibration from the electric motor 66 to the grip 65 are approximately illustrated, and the other elements constituting the other structures are omitted. In the present variation example, elements specified by the same reference numbers carry out the same operations, and a duplicate description of such elements will be omitted.

As shown in FIGS. 9 and 10, in the present variation example, a relaying gear 131 attached to the motor shaft 77, a relaying gear 132 engaging with the relaying gear 131, and a relaying gear 133 engaging with the relaying gear 132 constitute a driving force transmitting section 130. The proximal end of the driving shaft 68 is connected to the driving gear 133.

The coupling member 95 includes a base fixing portion 135 to which the base member 80 is fixed, a driving source attaching portion 136 to which the electric motor 66 is attached, and a relay continuing portion 137 which continues between the base fixing portion 135 and the driving source attachment portion 136. In the present variation example, the dimension of the relay continuing portion 137 in the first perpendicular direction (the direction indicated by arrow Y1 in FIGS. 9 and 10) and the second perpendicular direction (the direction indicated by arrow Y2 in FIGS. 9 and 10) is smaller than the dimension of the relay continuing portion 98 of the first embodiment. Thus, the outer peripheral surface of the grip 65 extends in a manner such that there is no gap between the first-perpendicular-direction-side part thereof and the proximal-side case 86.

In the present variation example, since the dimension of the relay continuing portion 137 in the coupling member 95 in the first and second perpendicular directions is small, the electric motor 66 attached to the driving source attaching portion 136 is located to the second perpendicular direction side compared with the first embodiment. In other words, the electric motor 66 is located closer to the driving shaft 68 than in the first embodiment. Thus, the number of relaying gears (131, 132, 133), etc. between the electric motor 66 and the driving shaft 68 is reduced. As a result, transmissibility of the movement driving force from the electric motor 66 to the driving shaft 68 is improved, and transmissibility of the movement driving force to the fin 72, which is a movement section, is improved.

Also in the present variation example, the driving source-side abutting surface (abutting surface) 115, to which the electric motor 66 which is a driving source is abutted, is provided on the driving source attaching portion 136. In the cross section perpendicular to the longitudinal axis C, the driving source-side abutting surface 115 is formed in the shape of an arc around the drive axis M of the electric motor 66. The electric motor 66 is abutted to the driving source-side abutting surface 115 covering the range of 180 degrees or more in directions around the drive axis.

Also in the present variation example, the vibration receiving surface 117, which is formed in a shape of an arc around the longitudinal axis C in the cross section perpendicular to the longitudinal axis C, is provided in the base member 80. The base-side abutting surface (abutting surface) 118 that is abutted to the vibration receiving surface 117 from the outer peripheral direction side is provided in the base fixing portion 135 of the coupling member 95. In the cross section perpendicular to the longitudinal axis C, the base-side abutting surface 118 is formed in the shape of an arc corresponding to the vibration receiving surface 117. The base-side abutting surface 118 is abutted to the vibration receiving surface 117 of the base member 80 covering the range of 180 degrees or more in the directions around the longitudinal axis.

In the present variation example, the coupling member 95 extends up to the part located to the proximal direction side from the proximal end of the electric motor 66. Thus, the electric motor 66 is abutted to the driving source-side abutting surface 115 across the entire length in the axis parallel directions parallel to the longitudinal axis C. Thus, compared to the first embodiment, the vibration transmissibility from the electric motor 66 to the coupling member 95 will be improved, and the transmissibility of the vibration generated in the electric motor 66 to the grip 65 will be further improved.

In the present variation example, the coupling member 95 extends up to the part located to the proximal direction side from the proximal end of the electric motor 66, and thus, a vibration is transmitted from the base-side abutting surface 118 of the coupling member 95 to the vibration receiving surface 117 of the base member 80 at a location closer to the grip 65, compared with the first embodiment. Thus, compared to the first embodiment, the vibration transmissibility in the base member 80 from the vibration receiving surface 117 to the vibration transmitting surface 123 will be improved, and the transmissibility of the vibration generated at the electric motor 66 to the grip 65 will be further improved.

Figure 12:
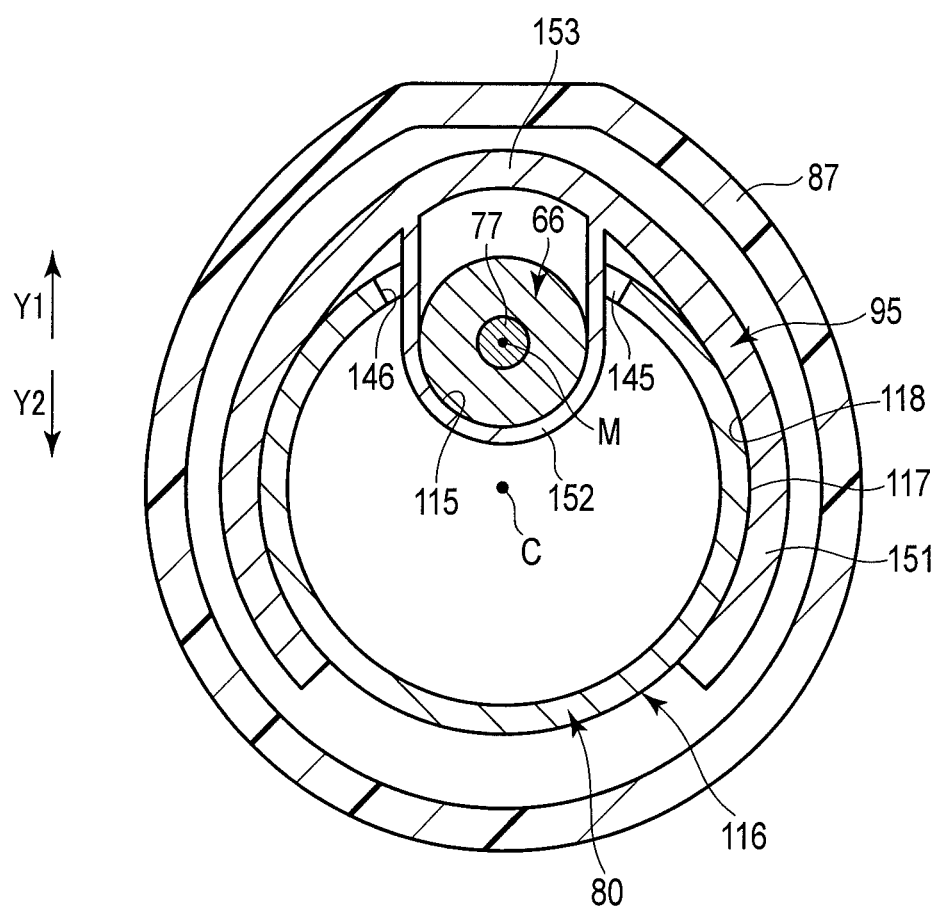
FIG. 12 is a cross-sectional view taken along line XII-XII in FIG. 9.

In the first embodiment and the first variation example, the electric motor 66, which is a driving source, is provided outside of the base member 80; however, the location to place the electric motor 66 is not limited thereto. For example, as shown in FIGS. 11 and 12 as the second variation example, the electric motor 66 may be provided to be inserted inside of the base member 80, as a second variation example. Herein, in the examples shown in FIGS. 11 and 12, only the elements essential for the structure for transmitting a movement driving force from the electric motor 66 to the driving shaft 68 and the structure for transmitting the vibration from the electric motor 66 to the grip 65 are approximately illustrated, and the other elements constituting the other structures are omitted. In the present variation example, elements specified by the same reference numbers carry out the same operations, and a duplicate description of such elements will be omitted.

As shown in FIGS. 11 and 12, in the present variation example, a relaying gear 141 which is attached to the motor shaft 77 and a relaying gear 142 engaging with the relaying gear 141 form a driving force transmitting section 140. The proximal end of the driving shaft 68 is connected to the driving gear 142.

In the present variation example, an opening defining surface 146 is provided in the base member 80. This surface 146 defines an opening 145 which opens toward the outside. The opening 145 opens toward the first perpendicular direction (the direction indicated by arrow Y1 in FIGS. 11 and 12). The opening width of the opening 145 is formed larger than the outer diameter of the second flexible tube section 25. For this reason, when manufacturing the endoscope 1, it is possible to insert the second flexible tube 25 into the inside of the base member 80 from the opening 145.

The coupling member 95 includes a base fixing portion 151 to which the base member 80 is fixed, a driving source attaching portion 152 to which the electric motor 66 is attached, and a relay continuing portion 153 which continues between the base fixing portion 151 and the driving source attachment portion 152. In the present variation example, the base fixing portion 151 and the relay continuous portion 153 are located outside of the base member 80, and the driving source attaching portion 152 is provided to be inserted inside of the base member 80 from the opening 145. Thus, the drive source attaching portion 152 is located to the second perpendicular direction (the direction indicated by arrow Y2 in FIGS. 11 and 12) side with respect to the opening 145.

In the present variation example, since the drive source attaching portion 152 is inserted inside of the base member 80, the electric motor 66 attached to the drive source attaching portion 152 is located to the second perpendicular direction side compared to the first embodiment and the first variation example. In other words, the electric motor 66 is located closer to the driving shaft 68 than the first embodiment and the first variation example. As a result, the number of relaying gears (141, 142), etc. between the electric motor 66 and the driving shaft 68 will be further decreased. Thus, the transmissibility of the movement driving force from the electric motor 66 to the driving shaft 68 is improved, and the transmissibility of the action driving force to the fin 72 which is a movement section is further improved.

Also in the present variation example, the driving source-side abutting surface (abutting surface) 115, to which the electric motor 66 which is a driving source is abutted, is provided in the driving source attaching portion 152. In the cross section perpendicular to the longitudinal axis C, the driving source-side abutting surface 115 is formed in the shape of an arc around the drive axis M of the electric motor 66. The electric motor 66 is abutted to the driving source-side abutting surface 115 covering the range of 180 degrees or more in the directions around the drive axis.

Also in the present example of variation, the vibration receiving surface 117, which is formed in the shape of an arc around the longitudinal axis C in the cross section perpendicular to the longitudinal axis C, is provided in the base member 80. The base-side abutting surface (abutting surface) 118 that is abutted to the vibration receiving surface 117 from the outer peripheral direction side is provided in the base fixing portion 151 of the coupling member 95. In the cross section perpendicular to the longitudinal axis C, the base-side abutting surface 118 is formed in the shape of an arc corresponding to the vibration receiving surface 117. The base-side abutting surface 118 is abutted to the vibration receiving surface 117 of the base member 80 covering the range of 180 degrees or more in the directions around the longitudinal axis.

In the present variation example, since the driving source attaching unit 152 is inserted inside of the base member 80, the electric motor 66 and the driving source-side abutting surface 115 are provided to be inserted inside of the base member 80 from the opening 145. A reduction in size and simplification in structure in the part between the grip 65 and the inserting section 2 can be realized by arranging the electric motor 66 inside of the base member 80.

In the present variation example, the driving source attaching portion 152 has a first dimension S1 in the axis parallel directions parallel to the longitudinal axis C. The base fixing portion 151 and the relay continuing portion 153 have a section dimension S2 in the axis parallel directions. The first dimension S2 is smaller than the second dimension S2. Thus, the driving source-side abutting surface 115 has the first dimension S1 in the axis parallel directions, and the base-side abutting surface 118 has the second dimension S2 in the axis parallel directions. In the present variation example, since the first dimension S1 of the driving source-side abutting surface 115 in the axis parallel directions is large, the abutting portion of the driving source-side abutting surface 115 to the electric motor 66 becomes larger than the abutting portion in the first embodiment. Thus, compared to the first embodiment, the vibration transmissibility from the electric motor 66 to the coupling member 95 will be improved, and the transmissibility of the vibration generated in the electric motor 66 to the grip 65 will be further improved.

In the first embodiment, the shaft member 102 is attached to the coupling member 95; however, the place to which the shaft member is attached is not limited thereto. For example, a shaft member (102) may be attached to the block body 110. In this case, a shaft engaging portion (106) with which a shaft member (102) engages will be provided in the coupling member 95. Accordingly, similar to the first embodiment, when the coupling member 95 is coupled to the block body 110, the relaying gear (base-side gear) 105 rotates about the gear axis G1 which is coaxial with the shaft member 102 and the relaying gear (driving source-side gear) 103.

In the aforementioned embodiment and variation example, the fin 72 of the attachment unit 30, which is attached to the inserting section 2, was explained; however, an example of a movement section is not limited to the fin 72. For example, the above-described configuration may be applied to the transmission of a movement driving force to a rotating body disclosed in Reference Document 1 (Jpn. Pat. Appln. KOKAI Publication No. 2012-245051). In this case, when the driving shaft 68 is rotated about the line core axis L as in the first embodiment, a movement driving force is transmitted to the rotating body. Upon transmission of the movement driving force to the rotating body, the rotating body moves toward the distal direction or the proximal direction. Furthermore, when the rotating body moves while a pressing force from a lumen wall is being applied to the rotating body toward the inner peripheral direction, a propulsive force is acted on the inserting section in a direction opposite to the moving direction of the rotating body. Accordingly, a movement section (72) should be provided in an inserting section (2) or an attachment unit (30) which is attached to the inserting section (2). If the movement section (72) is moved while a pressing force is applied to the movement section (72) toward the inner periphery direction, the propulsive force should act on the inserting section 2 in one of the axis-parallel directions parallel to the longitudinal axis C.

In the aforementioned embodiment and variation example, the endoscope device 1 was explained; however, an inserting device is not limited to the endoscope device 1. For example, the above-described configuration may be applied to an inserting section of a manipulator device which is an insertion device.

Therefore, the insertion device (1) includes: a cylindrical base member (80) which extends along the longitudinal axis (C) with the longitudinal axis (C) being an axial center; an inserting section (2) which is provided to a distal direction side with respect to the base member (80) and extends along a longitudinal axis; an movement section (72) which is provided in the inserting section (2) or an attachment unit (30) which is attached to the inserting section (2), and which moves to cause a propulsive force to act on the inserting section (2) in one of the axis-parallel directions parallel to the longitudinal axis (C) when the movement section (72) moves in a state that a pressing force acts toward an inner peripheral direction side; a driving source (66) which is provided in a manner such that a drive axis (M) of the driving source is parallel to the longitudinal axis (C), and is driven so as to generate a movement driving force to move the movement section (72); a line portion (68) which extends inside the inserting section (2) along a line core axis (L) parallel to the longitudinal axis (C), rotates about the line core axis (L) when the driving source (66) is driven, and transmits the movement driving force to the movement section (72); and a coupling member (95) which couples the driving source (66) to the base member (80), and transmits a vibration generated in the driving source (66) to the base member (80) in a state that the driving source (66) is caused to vibrate by a load acted on the movement section (72) when the movement section (72) moves; and a grip (65) which is coupled to the base member (80) and to which the vibration generated in the driving source (66) is transmitted from the base member (80).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An insertion device comprising:
   an inserting section which extends along a longitudinal axis;
   a movement section which is provided in the inserting section or an attachment unit which is attached to the inserting section, and which is configured to move to cause a propulsive force to act on the inserting section;
   a holdable grip which is provided to a proximal direction side with respect to the inserting section;
   a driving source which is configured to be driven so as to generate a movement driving force to move the movement section;
   a coupling member including a driving source-side abutting surface which abuts to an outer peripheral surface of the driving source; and
   a base member which abuts to the coupling member and the grip, the driving source being configured to vibrate due to a load acted against the movement section in a moving state in which the movement section moves by the transmitted movement driving force so that a vibration generated in the driving source is transmitted to the base member through the coupling member and then the vibration transmitted to the base member is transmitted to the grip, the base member including a vibration transmitting surface which abuts to an inner peripheral surface of the grip, the vibration transmitting surface being provided in a shape of an arc around the longitudinal axis in a cross section perpendicular to the longitudinal axis.

2. The insertion device according to claim 1, wherein the base member is made of a metal.

3. The insertion device according to claim 2, wherein the coupling member is made of a metal.

4. The insertion device according to claim 1, wherein the coupling member is made of a metal.

5. The insertion device according to claim 1, wherein the base member includes a vibration receiving surface in a shape of an arc around the longitudinal axis in a cross section perpendicular to the longitudinal axis of the base member, and
   the coupling member includes a base-side abutting surface which abuts to the vibration receiving surface from an outer peripheral direction side and which is configured to transmit the vibration generated in the driving source to the vibration receiving surface, the base-side abutting surface being provided in a shape of an arc corresponding to the vibration receiving surface in the cross section perpendicular to the longitudinal axis.

6. The insertion device according to claim 5, wherein the base-side abutting surface is abutted to the vibration receiving surface covering the range of 180 degrees or more in directions around the longitudinal axis.

7. The insertion device according to claim 1, wherein the driving source-side abutting surface of the coupling member has a first dimension in axis-parallel directions parallel to the longitudinal axis, and the vibration generated in the driving source is configured to be transmitted from the driving source to the driving source-side abutting surface, and
   the coupling member includes a base-side abutting surface to which the base member is abutted, and which is configured to transmit the vibration to the base member, the base-side abutting surface having a second dimension smaller than the first dimension in the axis parallel directions.

8. The insertion device according to claim 1, wherein the vibration generated in the driving source is configured to be transmitted from the driving source to the driving source-side abutting surface of the coupling member, and
the base member includes an opening defining surface which defines an opening, the opening opening toward an outside of the base member, the driving source-side abutting surface and the driving source being inserted to an inside of the base member from the opening.

9. The insertion device according to claim 1, wherein the base member is configured to transmit the vibration generated in the driving source toward a proximal direction, and
the grip extends along the longitudinal axis of the base member, and is attached to the base member from a proximal direction side.

10. The insertion device inserting section according to claim 1, wherein
the grip includes an abutting surface which is provided in a shape of an arc corresponding to the vibration transmitting surface in the cross section perpendicular to the longitudinal axis.

11. The insertion device according to claim 1, further comprising:
a line portion which extends inside the inserting section along a line core axis parallel to a longitudinal axis of the base member, the line portion being configured to rotate about the line core axis when the driving source is driven, and thereby configured to transmit the movement driving force to the movement section; and
a driving force transmitting section which is configured to transmit the movement driving force generated in the driving source to the line portion.

12. The insertion device according to claim 11, further comprising a block body which is attached to the base member,
wherein the driving force transmitting section comprises:
a driving source-side gear which is attached to the coupling member and which is configured to rotate upon transmission of the movement driving force; and
a block-side gear which is attached to the block body and which is configured to rotate about a gear axis coaxial with the driving source-side gear upon transmission of the movement driving force.

13. The insertion device according to claim 12, further comprising:
a shaft member which is attached to one of the coupling member and the block body, and which is configured to rotate about the gear axis integrally with the driving source-side gear and the block-side gear upon transmission of the movement driving force; and
a shaft engaging portion which is provided in the other one of the coupling member and the block body, and couples the block body to the coupling member by engaging the shaft engaging portion with the shaft member.

14. The insertion device according to claim 1, wherein the driving source is an electric motor which is driven when an electric power is supplied, and
the electric motor includes a motor shaft which rotates about a drive axis when the electric motor is driven.

15. The insertion device according to claim 10, wherein the abutting surface of the grip abuts to the vibration transmitting surface from an outer peripheral direction side, and the vibration generated in the driving source is configured to be transmitted from the vibration transmitting surface to the abutting surface of the grip.

* * * * *